United States Patent [19]

Yuda et al.

[11] Patent Number: 4,778,388
[45] Date of Patent: Oct. 18, 1988

[54] ROOT CANAL POSTS

[75] Inventors: Sadayuki Yuda, Suita; Takashi Kobayashi, Mino, both of Japan

[73] Assignee: Sankin Kogyo Kabushiki Kaisha, Osaka, Japan

[21] Appl. No.: 108,119

[22] Filed: Oct. 14, 1987

[30] Foreign Application Priority Data

Nov. 7, 1986 [JP] Japan .................................. 61-266439

[51] Int. Cl.⁴ ............................................. A61C 5/08
[52] U.S. Cl. ................................................... 433/221
[58] Field of Search ........................................ 433/221

[56] References Cited

U.S. PATENT DOCUMENTS 3,790,507  2/1974  Hodosh ............................... 433/173
3,863,344  2/1975  Pillet .................................... 433/173
4,016,651  4/1977  Kawahara ............................ 433/174
4,270,905  6/1981  Mohammed ......................... 433/173
4,525,145  6/1985  Scheicher ............................ 433/173
4,622,012  11/1986 Smoler ................................. 433/221

Primary Examiner—Robert Peshock
Attorney, Agent, or Firm—Oblon, Fisher, Spivak, McClelland & Maier

[57] ABSTRACT

A root canal post for use in constructing a therapeutic foundation on the root tooth for treatment of a broken tooth, the post comprising a head, a shank and a bore axially produced through the head and shank, the bore including a filler releasably filled therein so that after the post is anchored in the tooth, a subsequent treatment for a possible secondary cavities is applied through the bore which is made empty by removing the filler.

9 Claims, 3 Drawing Sheets

ROOT CANAL POSTS

BACKGROUND OF THE INVENTION

1. Field of the Invention

The present invention relates to a root canal post used for treatment of a broken tooth, and more particularly to a root canal post for such use, which is provided on a root tooth to construct a therapeutic foundation with the use of a pasty filler, such as composite resins. In this specification the term "root canal post" includes not only screw posts and molded posts but also auxiliary screw pins for supporting them; hereinafter the term "screw post" is used to represent all other posts.

2. Description of the Prior Art

In order to construct a therapeutic foundation for treatment of a broken tooth, it is known in the art to use a cast metal for it but recently the intracoronal therapy employing composite resins has drawn dentists' attention because of the advantage that the composite resins simultaneously form both the foundation and a post. However the construction of composite resins is fragile as compared with the conventional cast metal; therefore, to compensate for the reduced strength, a screw post is used to reinforce the foundation of composite resins.

In order to explain the background more clearly, referring to FIG. 5, the conventional practice will be described in detail:

The reference numeral 4 denotes a tooth root whose canal has been treated. After the surfacial softening dentitum is removed, a hole 3a is bored by means of a dental drill of a size corresponding to that of a screw post 1 while the retainer is being removed from the root canal. The hole 3a is filled with a dental cement 5, and simultaneously the screw post 1 is forced into the hole 3a. The screw post 1 has threads 1a whereby it is securely anchored in the hole 3a. Optionally the screw post 1 is reinforced by a screw pin 2 inserted into the tooth root. Then a composite resin 9 is applied to cover the screw post 1, and allowed to harden. The contour of the bulge of the resin is shaped by means of a diamond point so as to be adapted for the tooth root 4. Finally an artificial crown 8 is fitted.

However dental cavities are likely to occur again in the treated tooth. In such cases it will be required to withdraw the screw post 1, which, however, is very difficult or almost impossible to do because of the firm anchorage of it in the bed of cement 5. As a result, the tooth must be wholly extracted. In general the intracoronal treatments are expensive, but if the treatment of a secondary infection (secondary cavity) is required any price spent on the previous treatment will be wasted.

OBJECTS AND SUMMARY OF THE INVENTION

The present invention aims at solving the problems pointed out above, and has for its object to provide a root canal post which allows a possible disease in the root canal to be treated without removing the same.

Other objects and advantages of the present invention will become more apparent from the following detailed description, when taken in conjunction with the accompanying drawings which show, for the purpose of illustration only, one embodiment in accordance with the present invention.

According to the present invention there is provided a root canal post which comprises a head, a shank and a bore axially produced through the head and shank, the bore including a filler releasably filled therein so that after the post is anchored in the tooth, a subsequent treatment for a possible secondary caries is applied through the bore which is made empty by removing the filler.

DETAILED DESCRIPTION OF THE PREFERRED EMBODIMENT

Figure 1:
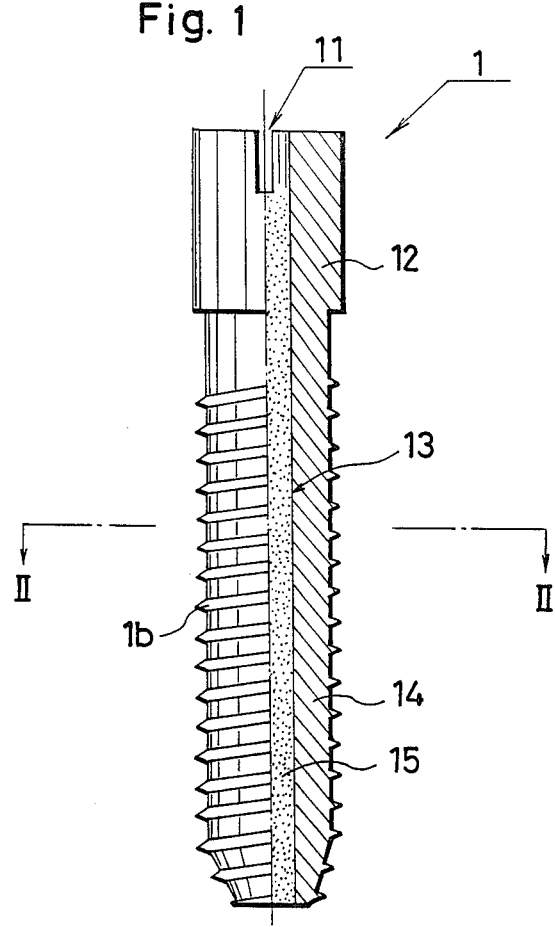
FIG. 1 is a partially cross-sectional view showing a root canal post embodying the present invention.
Figure 2:
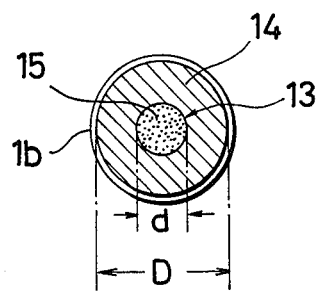
FIG. 2 is a cross-sectional view taken along the line II—II in FIG. 1.
Figure 3:
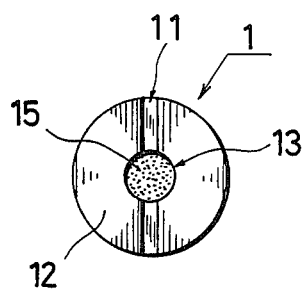
FIG. 3 is a plan view showing the root canal post of FIG. 1.

Referring to FIGS. 1 to 3 a root canal post 1 of the present invention comprises a shank 14 insertable in hole 3a and a head 12 which extends out of the hole, the shank 14 including helical projections 1b produced on its surface as thread forming means, and the head 12 including a slot 11 in which a rotating tools such as a screwdriver is fitted.

The post 1 has a bore 13 axially produced through the head 12 and the shank 14. The bore 13 has a filler 15 releasably filled, which is made of a non-toxic substance, such as fatty acid polyester, polylactic acid or any other polymers containing ester linkage,or else,collagen,starch,chitin or rubber(natural or synthetic). It is essential that if the filler is accidentally swallowed in the stomach, it is readily decomposed there. The substance for filler 15 can be solid, liquid or pasty.

When any treatment of a possible secondary cavity is required for the finished tooth the filler 15 is removed by a dental reamer or a file so as to empty the bore 13. The treatment is carried out to the root canal through the empty bore 13.

The root canal post 1 is made of stainless steel, gold, silver, palladium alloys, or ceramics. Depending upon the strength of the adopted material a ratio of the diameter (d) of the bore 13 to the outside diameter (D) of the shank 14, and the cross-sectional shape of the bore 13 are determined.

Figure 4A:
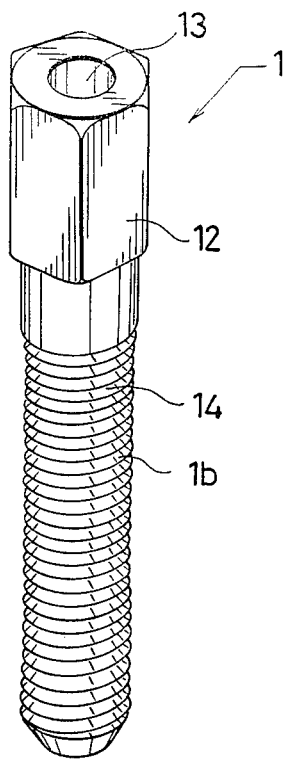
FIGS. 4(A) to (D) are perspective views showing various modified versions of the root canal post of the present invention.
Figure 4B:
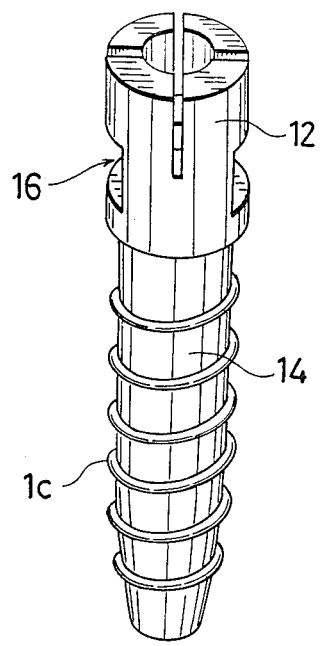
Figure 4C:
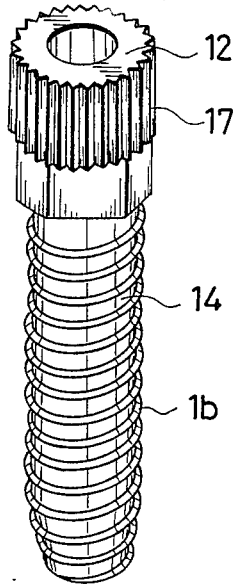
Figure 4D:
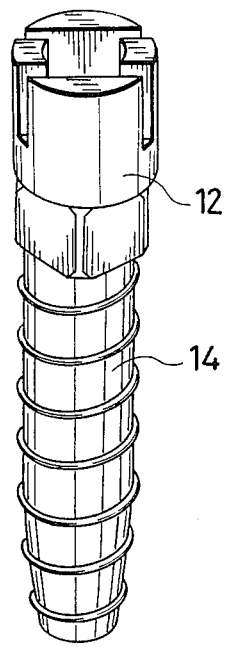
Figure 5:
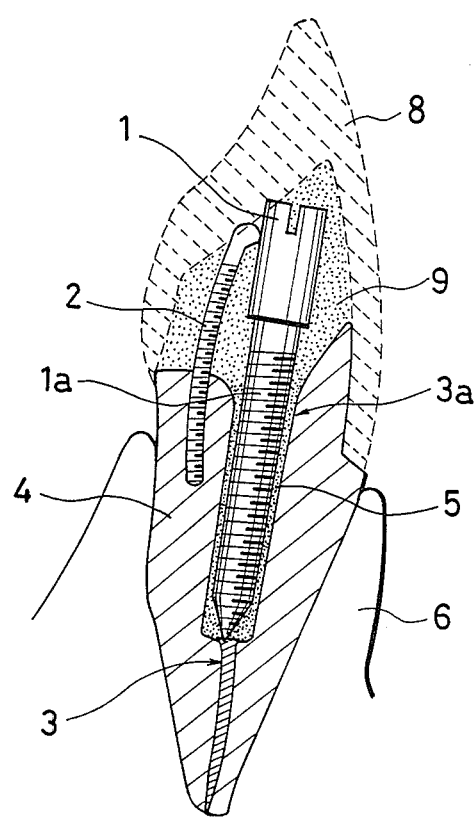
FIG. 5 is a cross-sectional view showing an state of the known root canal post anchored in the tooth.

FIGS. 4(A) to (D) show various modifications to the shapes of the head 12 and the slot 11. The head 12 can be hexagonal as shown in FIG. 4(A), and the slot 11 can be cross-like as shown in FIG. 4(B). The embodiment of FIG. 4(B) is additionally provided with recesses 16. The embodiment of FIG. 4(C) is provided with ridges 17 on its peripheral surface. Instead of the helical projections 1b a plurality of ring-shaped projections 1c can be provided at relatively large intervals as shown in FIG. 4(B).

What is claimed is:

1. A root canal post for use in constructing a therapeutic foundation on a tooth root, comprising:
   a shank for insertion into a hole in a tooth root;
   a head for extending out of said hole, said head and shank being united in a single body;
   a bore provided axially through both said head and shank; and a non-toxic releasable filler filling the entirety of said bore, whereby said filler may be removed to acquire access to said hole.

2. A root canal post as defined in claim 1, wherein the head includes a slot in its head so that a tool is fitted therein to rotate the post.

3. A root canal post as defined in claim 1, wherein the shank includes helical projections on its surface.

4. A root canal post as defined in claim 1, wherein the shank includes a plurality of ring-shaped projections at intervals.

5. A root canal post as defined in claim 1, wherein the filler contains polymers containing ester linkages.

6. A root canal post as defined in claim 1, wherein the filler contains collagen.

7. A root canal post as defined in claim 1, wherein the filler contains starch.

8. A root canal post as defined in claim 1, wherein the filler contains chitin.

9. A root canal post as defined in claim 1, wherein the filler contains rubber.

* * * * *